(12) United States Patent
Chin

(10) Patent No.: US 7,288,096 B2
(45) Date of Patent: Oct. 30, 2007

(54) APPARATUS FOR PLACEMENT OF CARDIAC DEFIBRILLATOR AND PACER

(75) Inventor: Albert K. Chin, Palo Alto, CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 10/369,980

(22) Filed: Feb. 18, 2003

(65) Prior Publication Data

US 2004/0143284 A1   Jul. 22, 2004

Related U.S. Application Data

(63) Continuation-in-part of application No. 10/346,663, filed on Jan. 17, 2003, and a continuation-in-part of application No. 10/347,212, filed on Jan. 17, 2003.

(51) Int. Cl.
*A61B 19/00* (2006.01)

(52) U.S. Cl. .................. 606/129; 606/108; 606/192; 606/194

(58) Field of Classification Search ................ 606/32, 606/41, 48, 129; 60/108, 129, 192, 194
See application file for complete search history.

(56) References Cited

U.S. PATENT DOCUMENTS

| | | |
|---|---|---|
| 207,932 A | 9/1878 | Alvord |
| 702,789 A | 6/1902 | Gibson |
| 1,727,495 A | 9/1929 | Wappler |
| 1,867,624 A | 7/1932 | Hoffman |
| 2,011,169 A | 8/1935 | Wappler |
| 2,028,635 A | 1/1936 | Wappler |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |

(Continued)

FOREIGN PATENT DOCUMENTS

DE    39 42 589    12/1989

(Continued)

OTHER PUBLICATIONS

Sabiston, David C., Jr., MD, Atlas of Cardiothoracic Surgery, ISBN 0-7216-3498-2, 1995.

(Continued)

*Primary Examiner*—Anhtuan T. Nguyen
*Assistant Examiner*—Charles H. Sam
(74) *Attorney, Agent, or Firm*—Faegre & Benson LLP

(57) ABSTRACT

Surgical procedure and surgical instruments include an electrode structure for insertion through tissue superiorly of a subxiphoid incision to a position posterior of an aspect of the sternum and anterior of the pericardium. The electrode structure may be expanded, for example, including an inflatable member to position a number of electrodes of the electrode structure in contact with the pericardium. Alternatively, an electrode structure on an insertion cannula may be retained in contact with the pericardium by the cannula positioned within the dissected tissue. Electrical conductors from the contacting electrodes are routed through the tract of dissected tissue toward the subxiphoid incision for attachment to a generator that is implanted in a subcutaneous pocket near the subxiphoid incision.

14 Claims, 6 Drawing Sheets

U.S. PATENT DOCUMENTS

| | | | |
|---|---|---|---|
| 3,357,433 | A | 12/1967 | Fourestier et al. |
| 3,856,016 | A | 12/1974 | Davis |
| 3,870,048 | A | 3/1975 | Yoon |
| 3,882,854 | A | 5/1975 | Hulka et al. |
| 3,920,024 | A | 11/1975 | Bowers |
| 3,934,115 | A | 1/1976 | Peterson |
| RE29,088 | E | 12/1976 | Shaw |
| 4,022,191 | A | 5/1977 | Jamshidi |
| 4,181,123 | A | 1/1980 | Crosby |
| 4,235,246 | A | 11/1980 | Weiss |
| 4,270,549 | A | 6/1981 | Heilman |
| 4,271,839 | A | 6/1981 | Fogarty et al. |
| 4,291,707 | A | 9/1981 | Heilman et al. |
| 4,318,410 | A | 3/1982 | Chin |
| 4,319,562 | A | 3/1982 | Crosby |
| 4,479,497 | A | 10/1984 | Fogarty et al. |
| 4,493,711 | A | 1/1985 | Chin et al. |
| 4,526,175 | A | 7/1985 | Chin et al. |
| 4,630,609 | A | 12/1986 | Chin |
| 4,662,371 | A | 5/1987 | Whipple et al. |
| 4,765,341 | A | 8/1988 | Mower et al. |
| 4,779,611 | A | 10/1988 | Grooters et al. |
| 4,784,133 | A | 11/1988 | Mackin |
| 4,863,440 | A | 9/1989 | Chin |
| 4,921,483 | A | 5/1990 | Wijay et al. |
| 4,957,477 | A | 9/1990 | Lundback |
| 4,991,578 | A | 2/1991 | Cohen |
| 5,033,477 | A | 7/1991 | Chin et al. |
| 5,071,428 | A | 12/1991 | Chin et al. |
| 5,129,394 | A * | 7/1992 | Mehra ................. 607/23 |
| 5,131,905 | A | 7/1992 | Grooters |
| 5,143,082 | A | 9/1992 | Kindberg et al. |
| 5,150,706 | A | 9/1992 | Cox et al. |
| 5,163,949 | A | 11/1992 | Bonutti |
| 5,183,464 | A | 2/1993 | Dubrul et al. |
| 5,215,521 | A | 6/1993 | Cochran et al. |
| 5,246,014 | A * | 9/1993 | Williams et al. ............ 607/122 |
| 5,256,132 | A | 10/1993 | Snyders |
| 5,271,380 | A | 12/1993 | Riek et al. |
| 5,318,589 | A | 6/1994 | Lichtman |
| 5,331,975 | A | 7/1994 | Bonutti |
| 5,334,150 | A | 8/1994 | Kaali |
| 5,336,252 | A | 8/1994 | Cohen |
| 5,339,801 | A | 8/1994 | Poloyko et al. |
| 5,373,840 | A | 12/1994 | Knighton |
| 5,376,076 | A | 12/1994 | Kaali |
| 5,385,156 | A | 1/1995 | Oliva |
| 5,391,156 | A | 2/1995 | Hildwein et al. |
| 5,433,198 | A * | 7/1995 | Desai ................. 600/374 |
| 5,437,680 | A | 8/1995 | Yoon |
| 5,464,447 | A | 11/1995 | Fogarty et al. |
| 5,482,925 | A | 1/1996 | Hutsell |
| 5,496,345 | A | 3/1996 | Kieturakis et al. |
| 5,514,153 | A | 5/1996 | Bonutti |
| 5,540,711 | A | 7/1996 | Kieturakis et al. |
| 5,551,947 | A | 9/1996 | Kaali |
| 5,569,183 | A | 10/1996 | Kieturakis |
| 5,569,291 | A | 10/1996 | Privitera et al. |
| 5,569,292 | A | 10/1996 | Scwemberger et al. |
| 5,571,161 | A | 11/1996 | Starksen |
| 5,591,192 | A | 1/1997 | Privitera et al. |
| 5,601,576 | A | 2/1997 | Garrison |
| 5,601,589 | A | 2/1997 | Fogarty et al. |
| 5,607,441 | A | 3/1997 | Sierocuk et al. |
| 5,613,937 | A | 3/1997 | Garrison et al. |
| 5,613,947 | A | 3/1997 | Chin |
| 5,618,287 | A | 4/1997 | Fogarty et al. |
| 5,634,895 | A | 6/1997 | Igo et al. |
| 5,650,447 | A | 7/1997 | Keefer et al. |
| 5,653,722 | A | 8/1997 | Kieturakis |
| 5,653,726 | A | 8/1997 | Kieturakis |
| 5,667,520 | A | 9/1997 | Bonutti |
| 5,669,927 | A | 9/1997 | Boebel et al. |
| 5,681,278 | A | 10/1997 | Igo et al. |
| 5,685,820 | A | 11/1997 | Riek et al. |
| 5,690,648 | A | 11/1997 | Fogarty et al. |
| 5,695,504 | A | 12/1997 | Gifford, III et al. |
| 5,702,343 | A | 12/1997 | Alferness |
| 5,702,417 | A | 12/1997 | Hermann |
| 5,707,390 | A | 1/1998 | Bonutti |
| 5,713,950 | A | 2/1998 | Cox |
| 5,716,392 | A | 2/1998 | Bourgeois et al. |
| 5,722,977 | A | 3/1998 | Wilhelmy |
| 5,725,492 | A | 3/1998 | Igo et al. |
| 5,728,148 | A | 3/1998 | Bostrom et al. |
| 5,730,756 | A | 3/1998 | Kieturakis |
| 5,738,628 | A | 4/1998 | Sierocuk et al. |
| 5,755,764 | A * | 5/1998 | Schroeppel ................. 607/122 |
| 5,755,765 | A | 5/1998 | Hyde et al. |
| 5,762,604 | A | 6/1998 | Kieturakis |
| 5,772,680 | A | 6/1998 | Kieturakis et al. |
| 5,797,946 | A | 8/1998 | Chin |
| 5,800,449 | A | 9/1998 | Wales |
| 5,810,878 | A | 9/1998 | Burel et al. |
| 5,827,216 | A | 10/1998 | Igo et al. |
| 5,860,997 | A | 1/1999 | Bonutti |
| 5,897,586 | A | 4/1999 | Molina |
| 5,900,433 | A | 5/1999 | Igo et al. |
| 5,902,331 | A | 5/1999 | Bonner et al. |
| 5,904,711 | A | 5/1999 | Flom et al. |
| 5,931,810 | A | 8/1999 | Grabek |
| 5,957,835 | A | 9/1999 | Anderson et al. |
| 5,957,880 | A | 9/1999 | Igo et al. |
| 5,972,010 | A | 10/1999 | Taheri |
| 5,972,013 | A | 10/1999 | Schmidt |
| 5,972,020 | A | 10/1999 | Carpentier et al. |
| 5,980,548 | A | 11/1999 | Evans et al. |
| 6,007,546 | A | 12/1999 | Snow et al. |
| 6,010,531 | A | 1/2000 | Donlon et al. |
| 6,030,406 | A | 2/2000 | Davis et al. |
| 6,036,714 | A | 3/2000 | Chin |
| 6,039,748 | A | 3/2000 | Savage et al. |
| 6,077,218 | A | 6/2000 | Alferness |
| 6,080,174 | A | 6/2000 | Dubrul et al. |
| 6,085,754 | A | 7/2000 | Alferness et al. |
| 6,095,968 | A | 8/2000 | Snyders |
| 6,096,064 | A | 8/2000 | Routh |
| 6,102,046 | A | 8/2000 | Weinstein et al. |
| 6,126,590 | A | 10/2000 | Alferness |
| 6,132,456 | A | 10/2000 | Sommer et al. |
| 6,156,009 | A | 12/2000 | Grabek |
| 6,162,195 | A | 12/2000 | Igo et al. |
| 6,165,183 | A | 12/2000 | Kuehn et al. |
| 6,206,004 | B1 | 3/2001 | Schmidt et al. |
| 6,237,605 | B1 | 5/2001 | Vaska et al. |
| 6,267,763 | B1 | 7/2001 | Castro |
| 6,287,250 | B1 | 9/2001 | Peng et al. |
| 6,322,536 | B1 | 11/2001 | Rosengart et al. |
| 6,346,074 | B1 | 2/2002 | Roth |
| 6,428,556 | B1 | 8/2002 | Chin |
| 6,463,332 | B1 | 10/2002 | Aldrich |
| 6,478,028 | B1 | 11/2002 | Paolitto et al. |
| 6,488,689 | B1 | 12/2002 | Kaplan et al. |
| 6,569,082 | B1 | 5/2003 | Chin |
| 6,607,547 | B1 | 8/2003 | Chin |
| 6,612,978 | B2 | 9/2003 | Lau et al. |
| 6,689,048 | B2 | 2/2004 | Vanden Hoek et al. |
| 6,697,677 | B2 | 2/2004 | Dahl et al. |
| 6,702,732 | B1 | 3/2004 | Lau et al. |
| 6,706,052 | B1 | 3/2004 | Chin |
| 6,835,193 | B2 | 12/2004 | Epstein et al. |
| 6,889,091 | B2 | 5/2005 | Hine et al. |
| 2002/0035361 | A1 | 3/2002 | Houser et al. |
| 2002/0052602 | A1 | 5/2002 | Wang et al. |

| | | | |
|---|---|---|---|
| 2002/0058925 | A1 | 5/2002 | Kaplan et al. |
| 2002/0111637 | A1 | 8/2002 | Kaplan et al. |
| 2002/0173622 | A1 | 11/2002 | Wettstein et al. |
| 2002/0177207 | A1 | 11/2002 | Sugiyama et al. |
| 2003/0212446 | A1 | 11/2003 | Kaplan et al. |

FOREIGN PATENT DOCUMENTS

| | | |
|---|---|---|
| EP | 0095727 A1 | 12/1983 |
| EP | 0 642 764 | 9/1994 |
| EP | 0791330 A2 | 8/1997 |
| FR | 1 370580 | 8/1964 |
| GB | 2 082 459 | 8/1981 |
| GB | 2 195 540 | 9/1987 |
| SU | 510235 | 4/1976 |
| SU | 1371689 | 3/1988 |
| WO | WO96/00038 | 4/1996 |
| WO | WO96/32882 | 10/1996 |
| WO | WO97/26831 | 7/1997 |
| WO | WO98/24378 | 6/1998 |
| WO | WO98/24488 A2 | 6/1998 |
| WO | WO98/24488 A3 | 6/1998 |
| WO | WO98/24488 | 11/1998 |
| WO | WO99/13785 | 3/1999 |
| WO | WO99/13936 | 3/1999 |

OTHER PUBLICATIONS

Bartoccioni, S., et al. Laparoscopic Harvesting of Right Gastroepiploic Artery for Coronary Artery Bypass Graft Performed Without Sternotomy [online], [retrieved on Oct. 5, 1999] Retrieved from the internet <URL:http://www.cstnet.org/doc/2628.

Benetti, Federico, et al., "Video Assisted Coronary Bypass Surgery", J Card Surgery, 1995, pp. 620-625.

Bernhard, Victor M. et al., "Cardiovascular Endoscopy: Historical Perspectives", Endovascular Surgery, 1989 W.B. Saunders Company, pp. 13-30.

Broadman, R. et al., "ICD Implantation via Thoracoscopy, "Mailslot" Thoracotomy, and Subxiphoid Incision," *The Annals of Thoracic Surgery*, vol. 57, No. 2, Feb. 1994, pp. 475-476.

Carpentier, A., "Technique d'implantation de pace-maker par une voie d'abord abdominate sous-xyphoidienne," *LaPresse Medicale*, Masson et Cie, Editeurs, Paris, vol. 76, No. 2, Jan. 13, 1968, 2 pp.

Comedicus Gets Approval to Sell Product in European union, Mar. 1, 1999, Swenson NHB Investor Relations, 4 pages.

De Feyter, P.J. et al., "Permanent Cardiac Pacing with Sutureless Myocardial Electrodes: Experience in First One Hundred Patients," *PACE*, vol. 3, No. 2, Mar. 1980, pp. 144-149.

Delaria, G.A. et al., "Leg Wound Complications Associated With Coronary Revascularization", J.Thorac. Cardiovasc. Surgery, 81:403-407, 1981.

Dimitri, W.R., et al., "A Quick and Atraumatic Method of Autologous Vein harvesting Using the Subcataneous Extraluminal Dissector", J. Cardiovasc. Surg., 28:103-11, 1987.

Fogarty, M.D., Thomas J., et al., "Selected Applications of Balloon Dissection", pp. 45-52.

Fontenelle, Larry, J., "Subxiphoid Pericardial Window", Thoracic and Cardiovascular Surgery, The American Association for Thoracic Surgery, Jul. 1971, vol. 62, No. 1, pp. 95-97.

Grandjean, Jan G., et al., "Coronary Reoperation via Small Laparotomy Using Right Gastroepiiploic Artery Without CPB", Society of Thoracic Surgeons, 1996, pp.

Hauer, G., et al, "Endoscopic Subfascial Discussion of Perforating Wein", Surg. Endos. 2:5-12, 1988.

Kaminski, Diane, "Firm Aims to Bypass Heart-piercing Treatments", Medical Industry Today, Medical Data International, Sep. 23, 1998.

"Incision Decision", Atrium Medical Corporation advertisement, appearing in J. Thorac. Cardiovasc. Surg., 83(4), 1982.

Kirklin, John W., et al., "Cardiac Surgery: Morphology, Diagnostic Criteria, Natural History, Techniques, Results, and Indications", vol. 2, Second Edition, 1993, Chapter 52, p. 1695.

Levin, Bradley H., "the Subxiphoid Pericardial Window", Surgery, Gynecology & Obstetrics, Dec. 1982, vol. 155, pp. 804-806.

Meldrum-Hanna, W. et al., "Long Saphenous Vein Harvesting," J. Surg., 56: 923-924, 1988.

Moazami, N., M.D. et al., "Minimally Invasive Greater Saphenous Vein harvesting For Coronary Artery Bypass Surgery", Mar. 1997, pp. 94-98.

Prager, Richard L. et al., "The Subxiphoid Approach to Pericardial Disease", The Annals of Thoracic Surgery, vol. 34, No. 1, Jul. 1982.

Rashid, A., et al., "Subcutaneous Technique for Saphenous Vein Harvest", Ann. Thorac. Surg., 37(2):169-170, 1984.

Santos, Gil H., et al., "The Subxiphoid Approach in the Treatment of Pericardial Effusion", Albert Einstein College of Medicine, Sep. 21, 1976, pp. 467-470.

"Saphenous Vein Grafts Are No. 1. Period," Atrium Medical Corporation advertisement, appearing in J. Thorac. Cardiovas. Surg., 82(6), 1981.

Simonsen, Michael, Ph.D., "Researchers Undaunted by Setbacks in the Angiogenesis Sector", American Health Consultants, vol. 5, No. 5, May 1999.

Spodick, David H., "Directly Applied Cardiac Therapy: Experts Explore Potential Benefits", Internal Medicine World Report, 1998.

Spodick, David H., "IPTD: Intrapericardial Therapeutics and Diagnostics: The PerDUCER Permits Direct Access to the Heart", Cath-Lab Digest, Sep. 1999, vol. 7, No. 9.

Stewart, S., M.D., "Placement of the Sutureless Epicardial Pacemaker Lead by the Sybxiphoid Approach," *The Annals of Thoracic Surgery*, vol. 18, No. 3, Sep. 1974, pp. 308-313.

The 4th International Symposium on Intrapericardial Therapeutics and Diagnostics, Mar. 8, 1999, New Orleans, Louisiana.

Watkins, Jr., L. M.D. et al., "Implantation of the Automatic Defibrillator: The Subxiphoid Approach," *The Annals of Thoracic Surgery*, vol. 34, No. 5, Nov. 1982, pp. 515-520.

Wheatley, D.J., M.D., ed., "Surgery of Coronary Artery Disease", C.V. Mosby Company, pp. 348-349, pp. 374-375.

Zenati M., M.D. et al., "Left Heart Pacing Lead Implantation Using Subxiphoid Videopericardioscopy," *J. Cardiovasc Electrophysiol*, vol. 14, Sep. 2003, pp. 949-963.

International Search Report and Written Opinion, PCT/US04/00859, Jun. 20, 2005.

International Search Report and Written Opinion, PCT/US04/00760, Jul. 6, 2005.

Myers, E. L. et al., "Tsg101, an Inactive Homologue of Ubiquitin Ligase E2, Interacts Specifically With Human Immunodeficiency Virus Type 2 Gag Polyprotein and Results in Increased Levels of Ubiquinated Gag," J. Virol, Nov. 2002, vol. 76, No. 22.

PCT International Search Report and Written Opinion; PCT/US04/34538, Nov. 3, 2005, 10 pages.

PCT International Search Report and Written Opinion; PCT/US04/34538, Nov. 3, 2005, 10 pages.

PCT International Search Report an Written Opinion, PCT/US04/00760, Sep. 27, 2006, 7 pages.

* cited by examiner

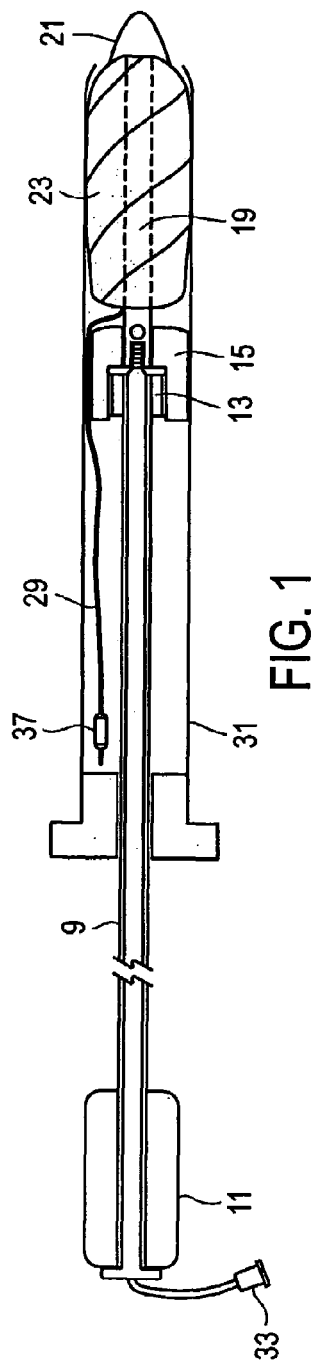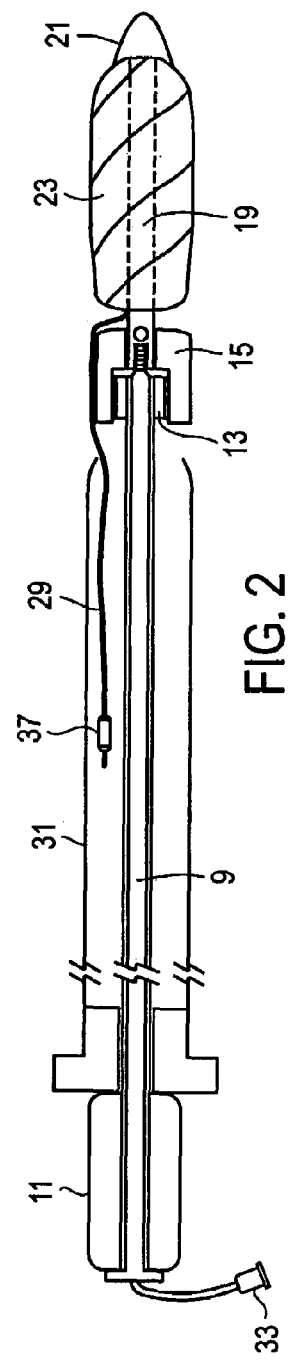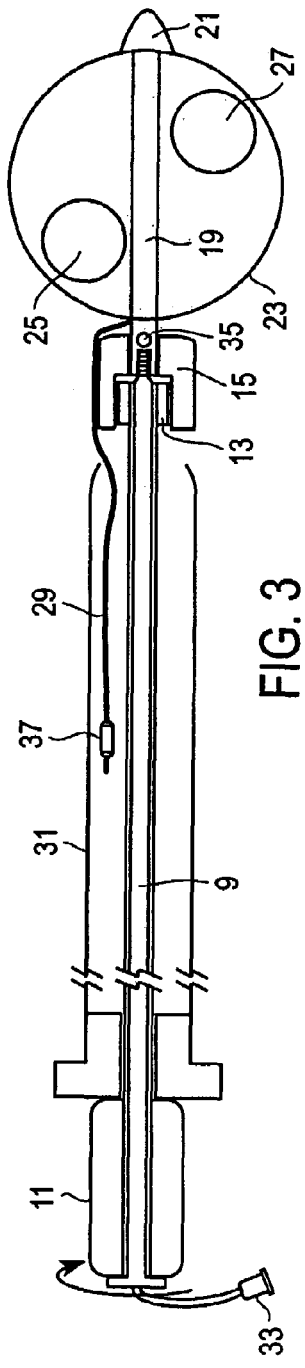

APPARATUS FOR PLACEMENT OF CARDIAC DEFIBRILLATOR AND PACER

RELATED CASES

This application is a continuation-in-part of application Ser. No. 10/346,663, entitled "Endoscopic Subxiphoid Surgical Procedures", filed on Jan. 17, 2003 by Albert K. Chin, and is a continuation-in-part of application Ser. No. 10/347,212 entitled "Apparatus and Method for Endoscopic Surgical Procedures" filed on Jan. 17, 2003 by Albert K. Chin, which applications are incorporated in their entireties herein by this reference thereto.

FIELD OF THE INVENTION

This invention relates to surgical instruments and procedures for placement of cardiac pacer or defibrillator electrodes, particularly via subxiphoid incision and insertion of an electrode structure in an extrapericardial position with a connected generator disposed in a subcutaneous pocket adjacent the subxiphoid incision.

BACKGROUND OF THE INVENTION

Contemporary surgical techniques for installing electrodes on the heart of a patient that is at risk for ventricular fibrillation or bradycardia arrhythmias commonly involves insertion of a wire electrode through the patient's venous system into the heart, and connection of the electrode to an implanted defibrillator or pacemaker. These procedures are commonly performed in a cardiac catheterization lab, under fluoroscopic x-ray guidance. It is desirable to place defibrillator or pacing electrodes in contact with the pericardium of the heart with minimal trauma and simple surgical techniques that can be rapidly implemented, with or without the need for fluoroscopic guidance.

SUMMARY OF THE INVENTION

In accordance with one embodiment of the present invention, an electrode structure includes an inflatable balloon having surface-oriented electrode patches for positioning extrapericardially at a posterior aspect of the sternum. The electrode structure is positioned via a subxiphoid incision and entry along a tract of dissected tissue to the posterior aspect of the sternum. Orientation of the electrode patches is gauged via radiological or mechanical techniques, and the balloon is inflated to engage the electrode patches on a surface thereof with selected regions of the pericardium. Surgical instruments for inserting and placing the electrode structure within the posterior aspect of the sternum are specifically configured to facilitate the placement via the subxiphoid entry. Associated electrical conductors are disposed substantially along the dissected tract to an implantable pacer or defibrillator that is inserted into a subcutaneous pocket formed adjacent the subxiphoid entry incision.

BRIEF DESCRIPTION OF THE DRAWINGS

FIG. 1 is a pictorial view of the instrument in accordance with one embodiment of the present invention;

FIG. 2 is a pictorial view of the instrument of FIG. 1 with the outer sheath retracted;

FIG. 3 is a bottom pictorial view of the instrument of FIG. 2 with the balloon-electrode structure inflated;

DETAILED DESCRIPTION OF THE INVENTION

Figure 5:
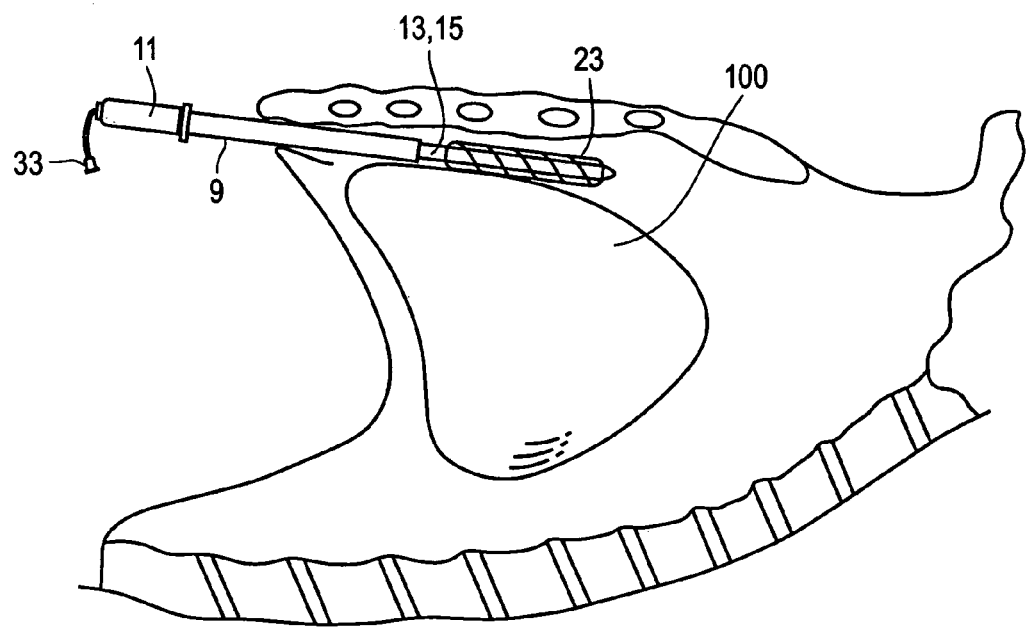
FIG. 5 is a side sectional view of the instrument of FIG. 2 in position within a patient.

Referring now to FIG. 1, there is shown a pictorial sectional view of one embodiment of the instrument in accordance with the present invention. Specifically, a central elongated hollow shaft 9 includes a handle 11 attached to the proximal end of the shaft 9, and includes a fitting or connector 13 on the distal end of the shaft 9. A mating connector 15 is detachably engaged with the connector 13, and is attached to the proximal end of a hollow support shaft 19 that includes a tissue-dissecting tapered tip 21 on the distal end. An inflatable member 23, preferably inelastic, as later described herein, is also supported on the shaft 19, and is shown furled or rolled around shaft 19 in an undeployed configuration. Electrically conductive patches 25, 27, as illustrated in the bottom views of FIGS. 3 and 4, include electrical conductors 29 that extend from the member 23 toward the proximal end of the shaft 9. An outer hollow sheath 31 is slidably mounted on the central shaft 9 and extends distally over the mating connectors 13, 15, and over the balloon or inflatable member 23 in undeployed configuration substantially to the base of the tapered tip 21. The cable of electrical conductors 29 is also confined within the outer sheath. A port 33 communicates with the hollow central shaft 9 for supplying fluid under pressure through the shaft 9 to the inflatable member 23 supported on shaft 19. The instrument illustrated in FIG. 1 is thus configured for insertion into a patient in a manner as later described herein, with the tapered tip 21 aiding advancement of the instrument through a tissue-dissected channel from the subxiphoid incision toward the anterior pericardium.

The proximal end of the support tube 19 may be internally threaded, and mating threads on the distal end of the central shaft 9 screw into the support tube to fix the balloon 23 onto the central shaft. The hub 15 attached to the proximal end of the support tube 19 includes a non-round cavity that mates with the corresponding connector 13 on the distal end of the central shaft. Thus, when the support shaft 19 and the central shaft 9 are screwed together, or are otherwise detachably connected, the assembly may be rotated, and torque may be transmitted to the tip 21 of the instrument for bluntly dissecting tissue. Keying of the connectors 13, 15 in this manner also preserves the orientation of the balloon 23 so that the patch electrodes 25, 27 can be properly oriented on the inferior surface of the balloon during placement thereof on the anterior pericardium. In one embodiment, the balloon 23 deflates upon detachment of the central shaft 9 from the support shaft 19. However, the balloon 23 stays in position on the anterior pericardium due to the conformance of the balloon 23 to the extra-pericardial cavity formed during balloon inflation. Similarly, frictional members or small protrusions can be disposed on the balloon 23 to maintain the position of the electrodes.

In another embodiment of the invention, a sealing valve may be added to the connector 15, such as a check-ball valve 35, to ensure that the balloon does not deflate upon detachment of the central shaft 9. The balloon retained in inflated configuration is less likely to migrate out of position after insertion. After several days to several weeks, the balloon may be deflated via percutaneous needle puncture in the intercostal space. Additionally, the balloon surface may be coated or covered with fabric or coarse-mesh material or other suitable material 50 that promotes fibrous adhesions to hold the balloon in place. Such coating or covering may be applied to the side opposite the patch electrodes 25, 27, or may be on both sides of the balloon except at the locations of the electrodes.

Referring now to FIG. 2, there is shown a pictorial sectional diagram of the instrument in FIG. 1 re-configured with the outer sheath 31 drawn back proximally to the handle 11 to expose the inflatable member 23 and the mating connectors 13, 15 between central shaft 9 and support shaft 19. In this configuration, the inflatable member 23 can be inflated with fluid (e.g., air or saline solution) under pressure to deploy the inflatable member 23, as illustrated in FIG. 3.

Figure 4:
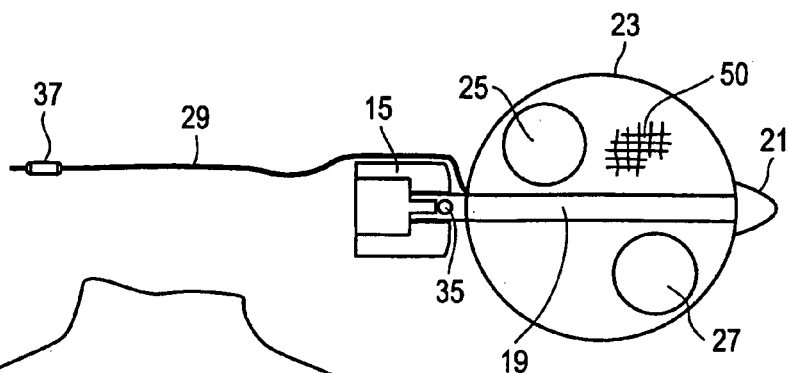
FIG. 4 is a bottom pictorial view of the electrode structure detached from the instrument.

The inflatable member 23 includes two substantially circular membranes of flexible but substantially inelastic material such as mylar or polyurethane that are bonded together substantially only around the periphery thereof (and to the support shaft 19) to form a disk-like balloon having an interior between the membranes that is disposed in fluid communication with the hollow support shaft 19. One disk-like surface of the member 23 supports one or more electrode patches 25, 27 that are spaced apart to form pericardium-engaging contact electrodes. The patch electrodes 25, 27 may include surface pads of sputtered metal or organic conductive compounds or mesh or spiral grids that are affixed to the outer surface of the posterior membrane, as shown in the bottom view of FIGS. 3 and 4. The space between the membranes may thus be pressurized to expand the thickness of the member 23. The mating connectors 13, 15 may include a check valve such as a spring-biased ball 35 against a valve seat in connector 15 for retaining fluid pressure within the member 23 once pressurized through the central shaft 9 and support shaft 19. Thereafter, the mating connectors 13, 15 are detached or disconnected, leaving in place the inflated member 23 with attached shaft 19, connector 15 and tip 21, as shown in FIG. 4. The cable 29 of electrical conductors connected to the electrode patches 25, 27 may be suitably routed, as discussed later herein, for connection via connector 37 to an implantable defibrillator or pacer unit 53.

Figure 6:
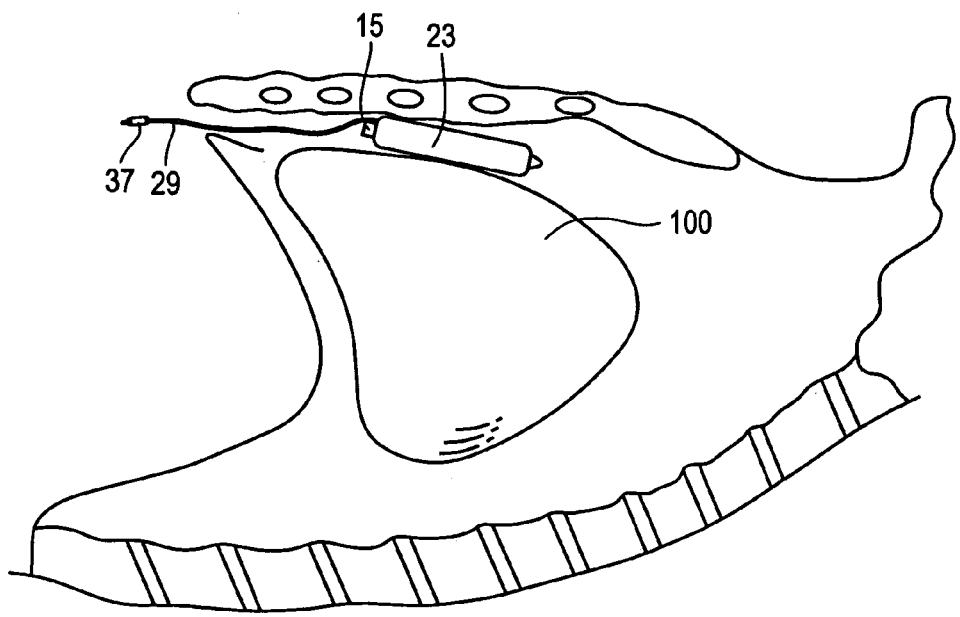
FIG. 6 is a side sectional view of the electrode structure of the instrument of FIG. 5 positioned within the patient.

Referring now to FIG. 5 there is shown a pictorial side view of the instrument of FIG. 1 being positioned within a patient. To place the instrument as shown, an incision of about 2 cm length is formed in the subxiphoid region, and blunt dissection is conducted to expose the linea alba, which is also incised a length of about 2 cm. A surgeon's gloved index finger is inserted in the incision in a superior direction, and a tract is bluntly dissected to the posterior aspect of the sternum. The finger is withdrawn, and the instrument in the configuration of FIG. 1 is inserted through the incision and advanced to dissect tissue along a path toward the posterior aspect of the sternum. The distal balloon 23 is constrained within the outer sheath 31 as the tapered tip 21 dissects tissue along the path. The maximal diameter of the portion of the instrument that is inserted into the body is approximately 10–12 mm, in the area of the sheathed balloon 23. The instrument is inserted without a sweeping motion, keeping the dissected tissue tract limited to about the 12 mm diameter of the instrument. Torsion about the long axis of the instrument may be employed to advance the instrument through tissue substantially in contact with the posterior aspect of the sternum. This allows the instrument to form a tract anterior to the anterior surface of the pericardium without poking the heart. The instrument is advanced until the balloon member 23 is centered on the anterior surface of the heart 100. Advancement of the instrument may be performed under fluoroscopic visualization oriented in a lateral direction to visualize the tip 21 in contact with the posterior aspect of the sternum and directed away from the heart 100. The instrument may be straight and rigid, as shown in FIG. 1. Once properly positioned, the outer sheath 31 of the instrument may be slid back along the central shaft proximally toward the handle 11 to expose the balloon member 23, as shown. The balloon member 23 is inflated to occupy the region between the posterior aspect of the sternum and the anterior pericardium, with the patch electrodes 25, 27 held resiliently in contact with the pericardium at selected locations, for example, adjacent the right atrium and the left ventricle. The central shaft 9 may then be detached from the support shaft 19 at the connectors 13, 15, leaving the member 23 pressurized in place (if connector 15 includes a check valve, as previously described), as illustrated in FIG. 6, or depressurized in place (if connector 15 does not include a check valve).

Figure 7A:
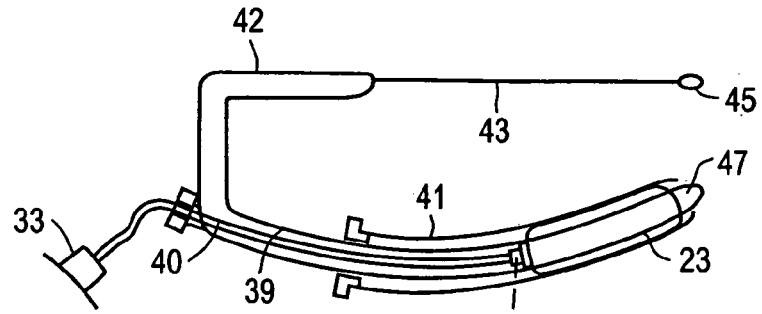
FIGS. 7A and 7B comprise a pictorial view of another embodiment of the instrument according to the present invention illustrating the curved configuration of the instrument.
Figure 7B:
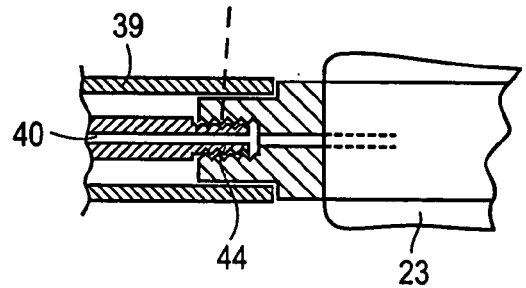
Figure 8:
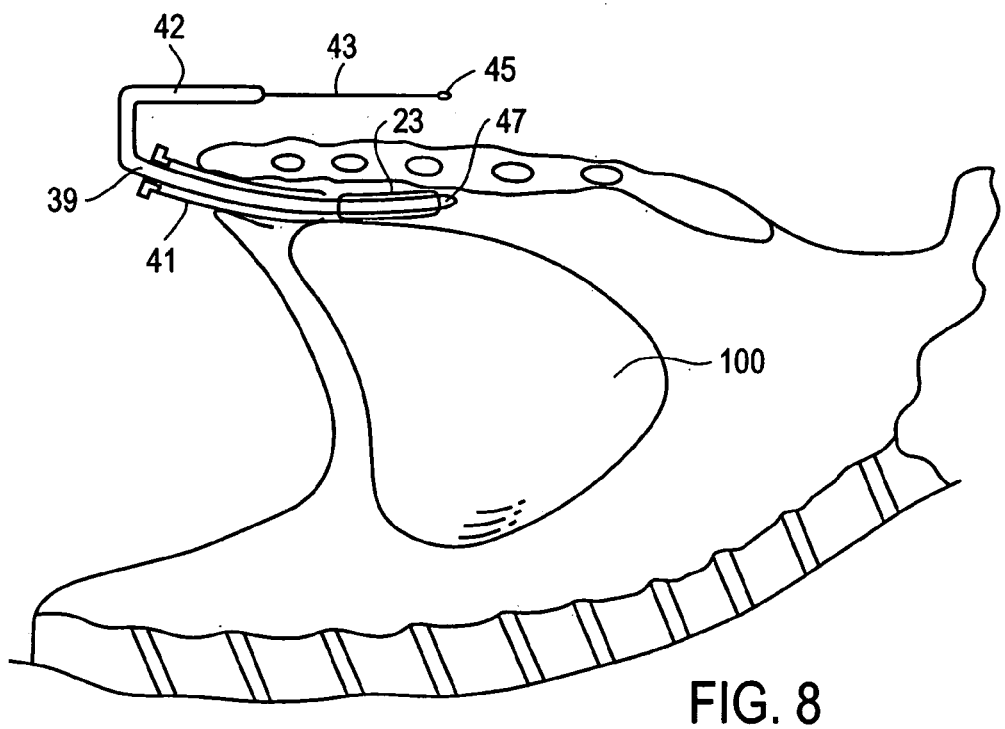
FIG. 8 is a side sectional view of the instrument of FIG. 7 positioned within a patient.

Another embodiment of the present invention, as illustrated in FIG. 7, facilitates placement of the inflatable member 23 without fluoroscopic guidance. Specifically, this configuration of the instrument includes a curved central shaft 39 and an outer sheath 41 of mating curve slidably mounted on the shaft 39 that is formed in a generally U-shape with the handle 42 extending up and forward ending generally parallel to the long axis of the shaft 39. An indicator 43 may extend from the handle (or the shaft 39 and handle 42 may extend) to position the tip 45 of the indicator, when in use, outside the body corresponding to the position of the tip 47 inside the body. The portion of the instrument for positioning inside the body is curved concave upwardly so that, as the instrument is advanced, the tip 47 is directed into contact with the posterior sternal surface, as shown in FIG. 8. A standard chest X-ray of the patient in an AP (anterior-posterior) orientation may be used initially to determine a desired position of the tip 47 of the instrument. The heart shadow in an AP chest X-ray and its position with respect to the rib cage and sternum can be noted with reference to a correct placement of the tip 47 of the instrument in order to position the balloon 23 and electrode pads 25, 27 on the heart. The patient's chest is palpated to count the ribs and delineate the sternal edge, and the desired spot for location of the tip 47 may be marked on the patient's skin. When the instrument is inserted through the subxiphoid incision and advanced superiorly, the external indicator 43, 45 aligns with the patient's skin marking, and the internal portion of the instrument including the balloon 23 is correctly placed.

Figure 9:
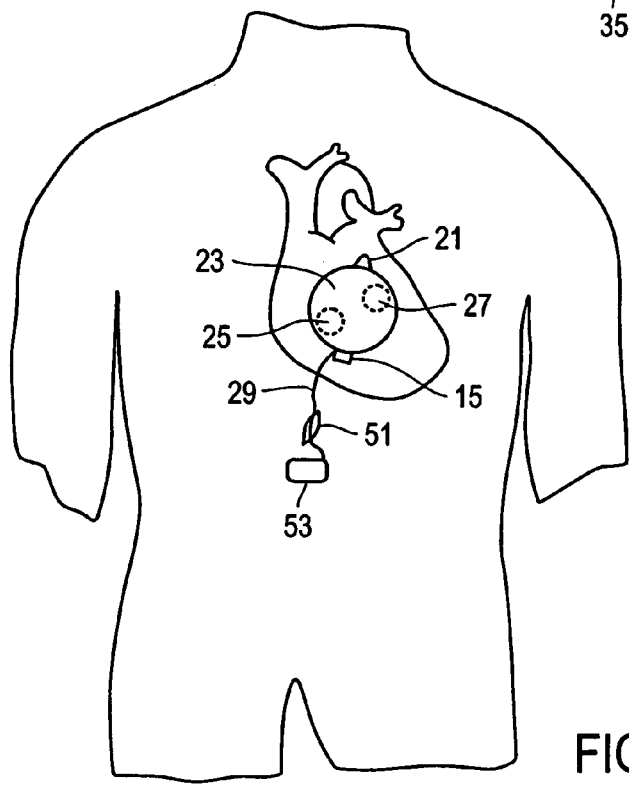
FIG. 9 is an illustration of the electrode structure according to the present invention positioned within a patient's body.

Once the instrument is advanced to the desired position, the sheath 41 is retracted to expose the balloon 23. The balloon is inflated to create a cavity anterior to the anterior portion of the pericardium. The balloon 23 contains two or more patch electrodes 25, 27, as previously described herein, that are oriented on the inferior side of the balloon. The balloon is substantially flat with an outer diameter of approximately 7–8 cm. Balloon inflation creates a cavity in adjacent tissue that conforms to the dimensions of the balloon 23 to hold the balloon 23 in the correct position against the heart 100, as shown in FIG. 9. Following balloon placement, the shaft 39 and handle 42 are detached from the balloon 23 by unscrewing the flexible mounting shaft 40 from the mating threaded connector 44 on the electrode structure to remove the central shaft 39 and sheath 41 and handle assembly 40, 42, 43 from the patient, leaving the balloon-oriented electrode structure 23 in place. Detachment of the mounting shaft 40 may facilitate deflation of the balloon 23 (in the absence of a check valve, as previously described herein), or may leave the balloon 23 inflated (with a check valve installed). The cable 29 of insulated conductive leads connected to the patch electrodes 25, 27 is routed through the tract of dissected tissue back to the subxiphoid incision 51, and is connected to the implantable generator 53 (pacer or defibrillator). The generator 53 is inserted into a subcutaneous pocket formed adjacent the subxiphoid incision 51.

Figure 10:
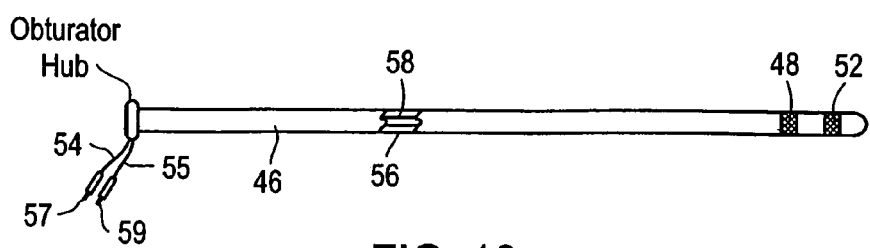
FIG. 10 is a partially cut away pictorial view of another embodiment of the present invention including a cannula-based electrode structure.

Referring now to FIG. 10, there is shown a partially cutaway pictorial view of another embodiment of the present invention in which a linear defibrillation or pacing cannula 46 of suitable flexibility may be advanced from a subxiphoid incision into position on the anterior pericardium. The cannula 46 may have two or more ring electrodes 48, 52 near its distal end, allowing conduction through the pericardium to the heart when the cannula 46 is positioned and the conductive leads 54, 55 from the ring electrodes 48, 52 are connected to the implantable generator 53. The circumferential ring electrodes 48, 52 ensure that electrical contact occurs with the anterior pericardium regardless of the angular orientation of the cannula 46 about its axis of elongation. The cannula 46 includes a central lumen 56 to accommodate a rigid obturator 58 that increases the stiffness of the cannula 46 and facilitates its advancement through tissue. Alternatively, the obturator may be disposed about the cannula as an outer sheath or tube. Conductive wires 54, 55 from the electrodes 48, 52 to the proximal end of the cannula 46 and connectors 57, 59 on the proximal end of the conductive wires 54, 55 interface with the generator unit 53 that is implanted near the subxiphoid incision, as previously described herein. Cannula insertion is performed by advancement in a straight line from the subxiphoid incision, without sweeping the cannula 46 back and forth. Torsion or twisting of the cannula 46 may be performed during insertion to facilitate advancement through tissue. Following insertion of the cannula 46 into position of the ring electrodes 48, 52 contacting the anterior pericardium, for example, in regions near the right atrium and left ventricle, the obturator 58 may be withdrawn from within the central lumen 56. Placement of the linear cannula 46 is simpler, as it does not require retraction of an overlying sheath or balloon inflation, and straight line insertion of the cannula 46 through tissue may adequately anchor the ring electrodes 48, 52 in contact with the anterior pericardium.

Figure 11A:
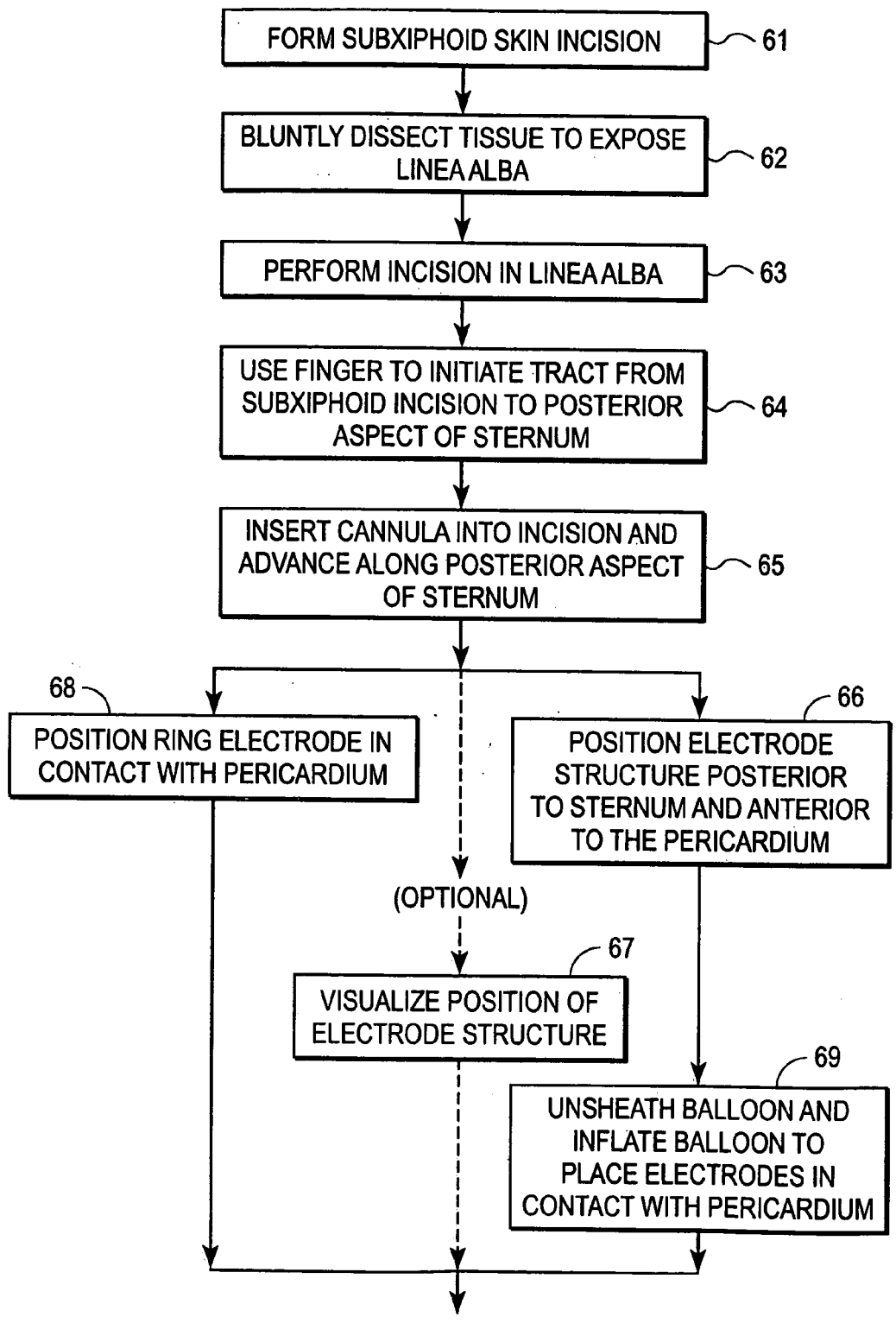
FIGS. 11A and 11B comprise a flow chart illustrating one method embodiment of the present invention.
Figure 11B:
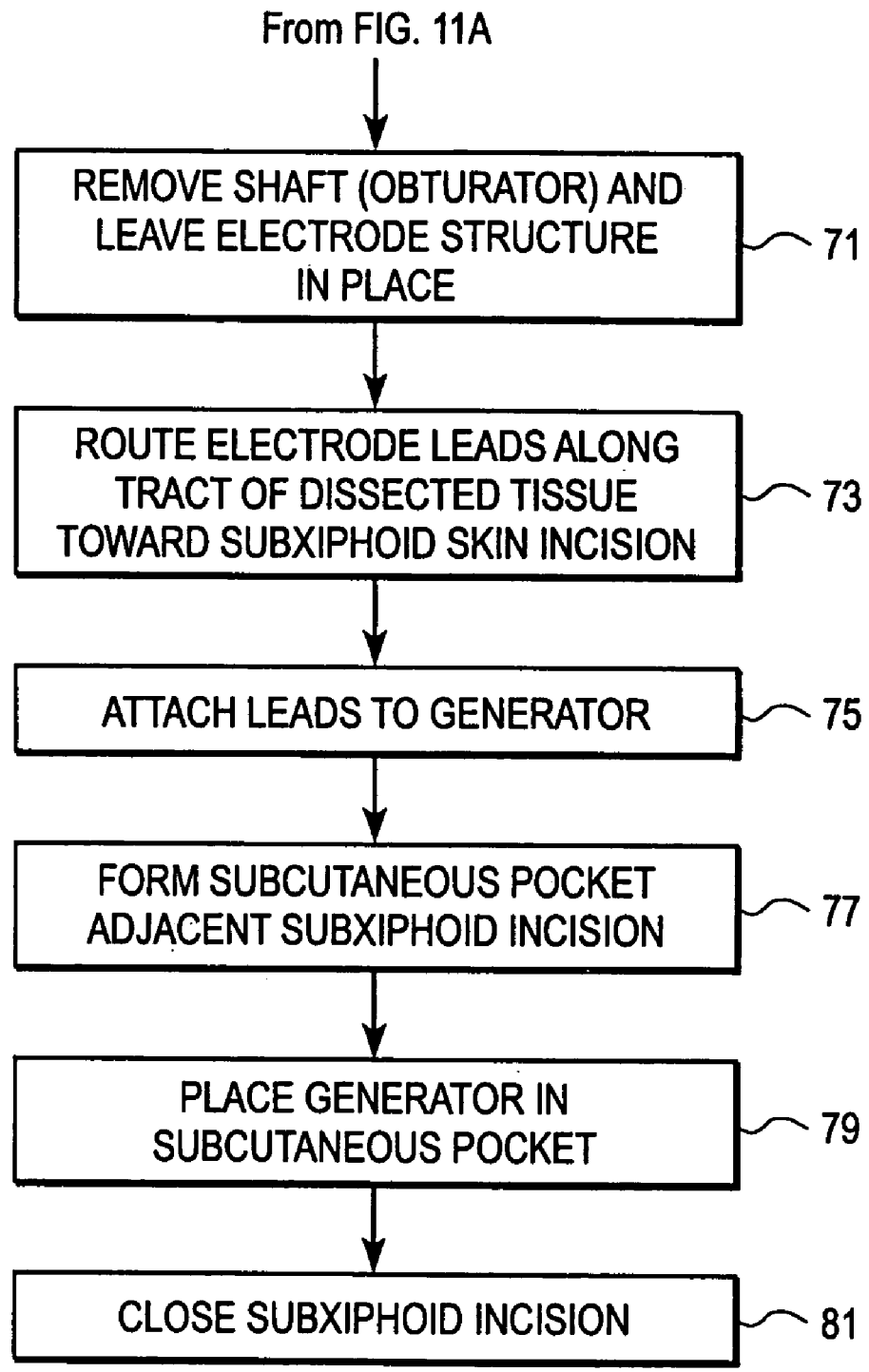

Referring now to the flow chart of FIGS. 11A and 11B, the procedure for placing an electrode structure in contact with the heart of a patient proceeds from initial formation of a subxiphoid entry incision 61. Blunt tissue dissection is performed to expose the linea alba 62 which is incised 63. The surgeon uses a gloved finger to dissect an initial tract 64 from the subxiphoid incision to the posterior aspect of the sternum. The instrument supporting the electrode structure, in a configuration as illustrated in FIG. 1 or 7 or 10, is inserted 65 into the initial tract and is advanced through tissue to a position posterior the sternum and anterior the anterior pericardium. The proper positioning of the instrument in an embodiment as illustrated in FIG. 1 or FIG. 10 can be verified 67 using such radiological visualization as fluoroscopy or x-ray imaging. Alternatively, proper positioning of the electrode structure may be accomplished without requiring radiological visualization and guidance of the instrument using the embodiment of the present invention in a configuration as illustrated in FIG. 7A. A standard chest x-ray of a patient in an AP orientation may be used initially to determine a desired position of the distal tip of the instrument. The heart shadow in such an x-ray image and its position relative to the rib cage and sternum can be designated for correct positioning of the distal tip and the associated electrodes for proper contact with the pericardium. The patient's skin may be marked to designate the correct positioning of the alignment tip 45 of the instrument in the configuration illustrated in FIG. 7A. Then, the instrument in this configuration is inserted through the subxiphoid entry incision, and is advanced superiorly until the external indicator 45 aligns with markings on the patient's skin to designate proper positioning of the electrode structure relative to the heart.

After the instrument in an embodiment of FIG. 1 or 7 is properly positioned posterior of the sternum and anterior of the anterior pericardium 66, the overlying sheath is slid back along the central shaft to expose 69 the electrode structure including the balloon 23 that supports the electrode pads 25, 27. The balloon is then inflated through the gas port 33 to expand the thickness of the electrode structure sufficiently to contact 69 the electrode pads 25, 27 with the anterior pericardium. Alternatively, the instrument in an embodiment of FIG. 7A is positioned 68 with the electrodes in contact with the pericardium. The proper position of the instrument can be verified, as previously described herein. Thereafter, the central shaft may be detached 71 from the electrode structure, leaving the balloon 23 and electrode pads 25, 27 in position, for removal of the central shaft and the overlying sheath from within the tract of dissected tissue. The removal of the sheath and central shaft of the positioning instrument also releases and positions 73 the cable of electrical conductors that are attached to the electrode pads within the tract of dissected tissue to extend toward the subxiphoid entry incision. These conductors are then attached to a generator 75. A subcutaneous pocket is formed 77 near the subxiphoid entry incision and the generator is implanted 79 in the subcutaneous pocket. The subxiphoid entry incision is then closed.

After the instrument in an embodiment of FIG. 10 is properly positioned posterior of the sternum and anterior of the anterior pericardium 68, the obturator 58 is withdrawn 71 from within the central lumen 56, leaving the ring electrode 48, 52 of the insertion cannula 46 in contact with the anterior pericardium. The conductive leads 54, 55 extend from the proximal end of the insertion cannula 46. These leads are positioned within the tract of dissected tissue 73 for attachment 75 to a generator, as previously described herein. A subcutaneous pocket is formed 77 adjacent the subxiphoid incision, and the generator with attached leads is placed within the pocket 79, and the subxiphoid incision is closed 81.

Therefore, the surgical instruments and surgical procedures for placing an electrode structure in contact with the heart advances an electrode structure through a subxiphoid access tract to a posterior aspect of the sternum and the anterior pericardium. The simplified surgical procedure using an embodiment of the present invention facilitates proper placement of the electrode structure with fluoroscopic visualization or x-ray positioning for minimal trauma to the patient. Conductive leads from contact electrodes of the electrode structure are routed along the access tract to the subxiphoid incision for connection to a pulse generator or defibrillator that is implanted within a subcutaneous pocket near the subxiphoid incision.

What is claimed is:

1. A surgical instrument comprising:
   an electrode structure including an inflatable member having substantially opposed surfaces and a number of electrodes disposed on one of the surfaces thereof, the inflatable member being disposed in uninflated configuration near a distal end of an elongated body; and
   a slide element carried by the elongated body to facilitate placement of the electrode structure in inflated configuration for contacting an external surface of the pericardium of a patient's heart with the number of electrodes on the inflatable member in an inflated configuration, the slide element being removable from the electrode structure following placement thereof and inflation of the inflatable member.

2. A surgical instrument comprising:
   an electrode structure including an inflatable member having substantially opposed surfaces and a number of electrodes disposed on one of the surfaces thereof, the inflatable member being disposed near a distal end of an elongated body;
   a sheath slidably supported on the body and overlaying the inflatable member for confining the inflatable member in uninflated configuration within the sheath in a distal slide position, and for exposing the inflatable member with the sheath in a proximal slide position; and
   a fluid passage within the body in communication with the inflatable member for inflating the inflatable member to facilitate contacting the number of electrodes on said one surface to an external surface of the pericardium of a patient's heart.

3. The surgical instrument according to claim 2 in which the opposed surfaces of the inflatable member include anterior and posterior membranes sealed together to form a pressurizable region therebetween, with at least two electrodes disposed in spaced relationship on the outer expandable surface of the posterior membrane for expansion away from the anterior membrane in response to pressurization of the region between membranes.

4. The surgical instrument according to claim 2 including a support shaft attached to the electrode structure that is detachable from the elongated body which includes a tissue-dissecting tapered tip on a distal end thereof.

5. The surgical instrument according to claim 2 including an electrical conductor connected to each of the number of electrodes and extending along the elongated body within the sheath.

6. The surgical instrument according to claim 4 including detachable mating connectors disposed on a proximal end of the elongated body and on a distal end of the support shaft for selectively connecting the shaft and body.

7. The surgical instrument according to claim 6 in which the mating connectors include a fluid passage therethrough for passing fluid under pressure through the elongated body to the pressurizable region between membranes of the inflatable member.

8. The surgical instrument according to claim 4 in which the elongated body and sheath slidable thereon are arcuately shaped in concave configuration with one portion of a generally U-shaped elongated body laterally spaced from, and extending in alignment with1 another portion thereof slidably supporting the sheath thereon.

9. The surgical instrument of claim 8 including an indicator tip extending along the laterally-spaced one portion of the body substantially in alignment with the tapered tip on the distal end of the elongated body.

10. An inflatable electrode structure for contacting the heart of a patient comprising:
    an anterior membrane and a posterior membrane of flexible substantially inelastic materials sealed together with a pressurizable region therebetween;
    a number of electrodes disposed in spaced relationship on an outer surface of the posterior membrane;
    an electrical conductor connected to each of the number of electrodes; and
    a fluid conduit in fluid communication with the pressurizable region for supplying fluid under pressure thereto to expand the spacing between the membranes.

11. The inflatable electrode structure according to claim 10 in which the fluid conduit includes an elongated body attached to at least one of the membranes and including a lumen therethrough in fluid communication with the pressurizable region between the membranes.

12. The inflatable electrode structure according to claim 11 in which the membranes are substantially circular and are sealed about the periphery to form the pressurizable region between the membranes within the periphery thereof.

13. The inflatable electrode structure according to claim 11 including a tapered tissue-dissecting tip disposed on a distal end of the elongated body, and on a proximal end thereof a detachable connector for supplying fluid under pressure to the pressurizable region.

14. The inflatable electrode structure according to claim 13 including on a portion of the outer surface of the posterior membrane not including the number of electrodes a material adapted for fibrous adhesion to a pericardium.

* * * * *

UNITED STATES PATENT AND TRADEMARK OFFICE
CERTIFICATE OF CORRECTION

PATENT NO. : 7,288,096 B2
APPLICATION NO. : 10/369980
DATED : October 30, 2007
INVENTOR(S) : Albert K. Chin It is certified that error appears in the above-identified patent and that said Letters Patent is hereby corrected as shown below:

<u>Page 3</u>
Line 12, delete "1988" and replace it with -- 1986 --
Line 35, delete "sybxiphoid" and replace it with -- subxiphoid --
Line 38, delete "Mar. 8" and replace it with -- Mar. 6 --

<u>Column 8, line 16</u>
Delete "with1" and replace it with -- with, --

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,288,096 B2 | Page 1 of 1 |
| APPLICATION NO. | : 10/369980 | |
| DATED | : October 30, 2007 | |
| INVENTOR(S) | : Albert K. Chin | |

It is certified that error appears in the above-identified patent and that said Letters Patent is hereby corrected as shown below:

Item (56) References Cited

Page 3
Foreign Patent Documents, Line 12, delete "1988" and replace it with -- 1986 --
Other Publications, Line 35, delete "sybxiphoid" and replace it with
-- subxiphoid --
Other Publications, Line 38, delete "Mar. 8" and replace it with -- Mar. 6 --

Column 8, line 16
Delete "with1" and replace it with -- with, --

This certificate supersedes the Certificate of Correction issued May 13, 2008.

Signed and Sealed this

Third Day of June, 2008

JON W. DUDAS
*Director of the United States Patent and Trademark Office*